United States Patent [19]

Mixson et al.

[11] Patent Number: Plant 6,372

[45] Date of Patent: Nov. 1, 1988

[54] ST. AUGUSTINE GRASS

[75] Inventors: Wayne C. Mixson, Apopka, Fla.; Terrance P. Riordan, Lincoln, Nebr.; Virgil D. Meier, Marysville, Ohio

[73] Assignee: The O. M. Scott & Sons Company, Marysville, Ohio

[21] Appl. No.: 893,960

[22] Filed: Aug. 7, 1986

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

A perennial St. Augustine grass having outstanding cold tolerance, along with good resistance to St. Augustine Decline Virus and gray leaf spot.

1 Drawing Sheet

BACKGROUND

A St. Augustine grass which has been named "Seville" was disclosed in U.S. Plant Pat. No. 4,097, which issued on Sept. 6, 1977.

SUMMARY OF THE VARIETY

This invention relates to a new and distinct perennial St. Augustine grass selected from the progeny of the controlled pollination of Seville with the pollen from a cold tolerant selection obtained from Memphis, Tenn. This yellow anther, white stigma genotype was labeled 6-72-99 and propagated vegetatively by stolons to provide planting stock for studying performance and making comparisons to present commercial varieties.

The excellent cold tolerance, good overall appearance, and good resistance to St. Augustine Decline Virus and gray leaf spot of 6-72-99 along with other information, allow this genotype to be distinguished from other St. Augustine grasses.

BRIEF DESCRIPTION OF THE ILLUSTRATIONS

DETAILED DESCRIPTION OF THE VARIETY

Figure 1:
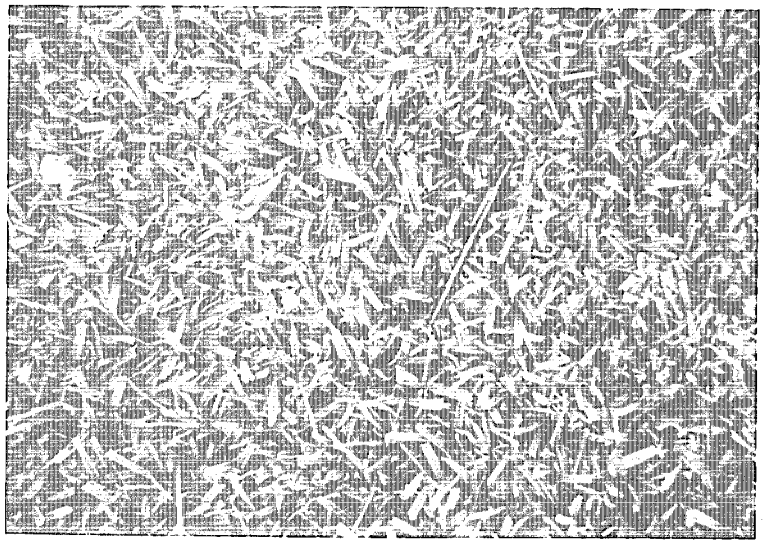
FIG. 1 is a photograph of 6-72-99 St. Augustine turf.
Figure 2:
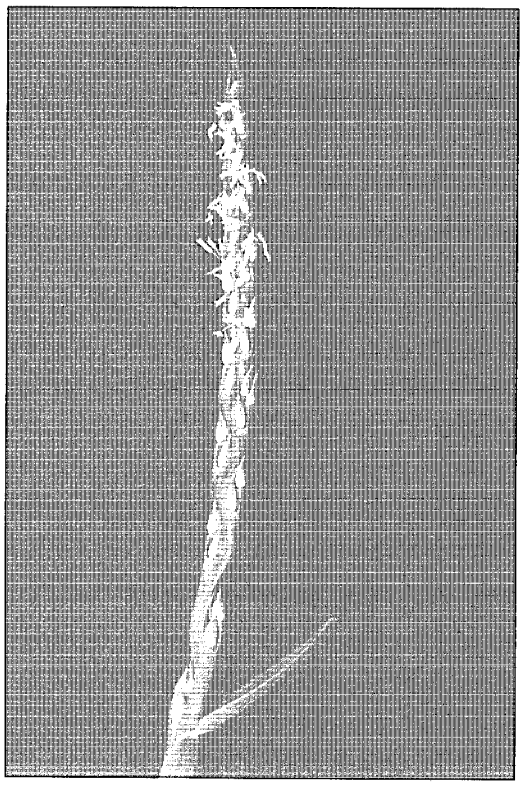
FIG. 2 shows a single spike of 6-72-99 St. Augustine grass plant depicting yellow anthers and white stigmas protruding from several spikelets.

Genotype 6-72-99 has a yellow anther color, a white stigma color, and an unreduced chromosome number of 18. The internodes are shorter and thicker than most commonly grown St. Augustine grass cultivars. Leaf blade length and leaf sheath length are significantly shorter than Floratam, a widely grown cultivar in Florida and Texas. The difference between 6-72-99 and Floratam in leaf blade length is accentuated under low light growing conditions. Floratam is noted for its poor shade performance in contrast to most St. Augustine grasses. The blade width of 6-72-99 is equal to or wider than other St. Augustine grasses. Measurements of the spike and related structures indicate that 6-72-99 has a longer spike, a longer peduncle, and a longer flag leaf sheath than other St. Augustine grasses except for Floratam. The chromosome numbers, anther and stigma color and morphological measurements of 6-72-99 and other St. Augustine grasses are compared in Tables 1, 2, 3 and 4.

TABLE 1

Chromosome numbers, anther color and stigma color of 6-72-99 and other St. Augustine grasses.

| Selection/Variety | Chromosome Number | Anther Color | Stigma Color |
|---|---|---|---|
| 6-72-99 | 18 | Yellow | White |
| Bitterblue | 27 | Yellow | Purple |
| Floratam | 27 | Yellow | Purple |
| Floratine | 27 | Yellow | Purple |
| Raleigh | 18 | Yellow | White |
| Seville | 18 | Yellow | Purple |
| Texas Common | 18 | Yellow | White |
| California Common | 18 | Yellow | White |
| 1081 | 18 | Purple | Purple |

TABLE 2

Comparative measurements of internode length and thickness of 6-72-99 and other St. Augustine grasses.

| Selection/Variety | Internode Length (cm) Florida[a] | Internode Length (cm) Ohio[b,c] | Internode Thickness (mm) Ohio[b] |
|---|---|---|---|
| 6-72-99 | 4.1 | 5.7 | 3.5 |
| Bitterblue | 3.7 | 6.9 | 2.7 |
| Floratam | 6.3 | 7.5 | 3.2 |
| Floratine | 4.7 | 5.8 | 2.7 |
| Raleigh | 5.8 | 7.0 | 3.2 |
| Seville | 4.5 | 6.8 | 2.7 |
| Texas Common | — | 6.2 | 3.0 |
| California Common | — | 4.2 | 2.4 |
| 1081 | 3.9 | 7.3 | 2.8 |
| LSD (.05) | 1.00 | 1.15 | .24 |

[a]Field planting - Fort Lauderdale, Florida. Average length of third to seventh internodes on terminal end of stolon.

[b]Greenhouse planting - Marysville, Ohio. Measurements taken on unclipped potted plants.

[c]Length of third internode from terminal end of stolon.

TABLE 3

Comparative Leaf Blade Length, Width and Sheath Length of 6-72-99 and other St. Augustine grasses.

| Selection/ Variety | Blade Length (cm) Texas[a] | Blade Length (cm) Ohio[b] High[c] Light | Blade Length (cm) Ohio[b] Low[d] Light | Blade Width[c] (cm) Ohio[b] | Sheath Length[c] (cm) Ohio[b] |
|---|---|---|---|---|---|
| 6-72-99 | 3.0 | 7.3 | 16.7 | 1.8 | 3.3 |
| Bitterblue | — | 7.4 | 17.5 | 1.5 | 2.8 |
| Floratam | 6.6 | 10.1 | 27.2 | 1.7 | 4.5 |
| Floratine | — | 8.6 | 16.3 | 1.4 | 3.2 |
| Raleigh | 3.9 | 7.8 | 13.8 | 1.7 | 3.7 |
| Seville | 2.9 | 6.9 | 18.4 | 1.4 | 2.9 |
| Texas Common | 2.7 | 8.1 | 16.6 | 1.7 | 3.6 |
| California Common | — | 3.8 | 11.8 | 1.2 | 2.2 |
| 1081 | — | 7.8 | 15.2 | 1.5 | 3.2 |

TABLE 3-continued

Comparative Leaf Blade Length, Width and Sheath Length of 6-72-99 and other St. Augustine grasses.

| Selection/ Variety | Blade Length (cm) Texas[a] | Ohio[b] High[c] Light | Ohio[b] Low[d] Light | Blade Width[c] (cm) Ohio[b] | Sheath Length[c] (cm) Ohio[b] |
|---|---|---|---|---|---|
| LSD(.05) | .77 | 2.03 | 3.25 | 0.17 | 0.71 |

[a]Field Planting - Cleveland, Texas.
[b]Greenhouse Planting - Marysville, Ohio. Measurements taken on unclipped potted plants.
[c]After a period of natural sunlight and a high level supplemental light.
[d]After a lengthy period of very cloudy conditions and no supplemental light.

TABLE 4

Comparative measurements of the inflorescence and related structures of 6-72-99 and other St. Augustine grasses[a].

| Selection/Variety | Spike Length (mm) | Spike Width (mm) | Peduncle Length (mm) | Peduncle Width (mm) |
|---|---|---|---|---|
| 6-72-99 | 93 | 5.3 | 68 | 2.1 |
| Bitterblue | 78 | 5.6 | 61 | 2.2 |
| Floratam | 96 | 5.9 | 83 | 2.4 |
| Floratine | 74 | 5.8 | 48 | 2.3 |
| Raleigh | 72 | 5.8 | 62 | 2.2 |
| Seville | 71 | 4.9 | 50 | 1.9 |
| Texas Common | 68 | 4.9 | 42 | 1.9 |
| 1081 | 78 | 5.2 | 60 | 1.9 |
| LSD(.05) | 10.0 | .64 | 18.3 | 0.28 |

| Selection/Variety | Flag Leaf Length (mm) | Flag Leaf Width (mm) | Flag Leaf Sheath Length (mm) |
|---|---|---|---|
| 6-72-99 | 21 | 6.7 | 46 |
| Bitterblue | 22 | 6.4 | 44 |
| Floratam | 35 | 6.3 | 46 |
| Floratine | 27 | 7.2 | 39 |
| Raleigh | 25 | 7.5 | 42 |
| Seville | 15 | 5.8 | 38 |
| Texas Common | 29 | 7.1 | 39 |
| 1081 | 25 | 6.3 | 39 |
| LSD(.05) | 12.4 | 1.08 | 6.7 |

[a]Greenhouse planting - Marysville, Ohio.

Field observations of 6-72-99 indicate that it has generally good turf quality characteristics throughout the year. However, it excels during the cooler winter and early spring months in its turf quality and its ability to avoid injury to occasional cold and freezing temperatures. These characteristics of 6-72-99 as compared with other St. Augustine grasses is illustrated in Tables 5, 6 and 7.

TABLE 5

Comparative turf quality[a] of 6-72-99 and other St. Augustine grasses at various locations in the U.S.

| Selection/ Variety | Turf Quality: Florida Apopka[b] | Florida Fort Lauderdale Expt 1[c] | Florida Fort Lauderdale Expt 2[d] | California SCFS[h] Expt 3[e] | California SCFS[h] Expt 4[f] | Somas[g] |
|---|---|---|---|---|---|---|
| 6-72-99 | 7.4 | 7.5 | 5.8 | 6.1 | 4.7 | 4.9 |
| Bitterblue | 6.2 | 5.6 | 5.9 | — | — | — |
| Floralawn | — | — | 7.1 | — | — | — |
| Floratam | 5.9 | 6.5 | 7.2 | — | 3.9 | — |
| Floratine | 6.2 | 5.3 | 6.2 | — | — | — |
| Raleigh | 6.6 | 3.0 | — | — | 3.6 | — |
| Seville | 7.8 | 7.3 | 6.3 | 6.7 | — | 5.3 |
| Texas Common | 7.5 | — | — | 5.9 | 4.5 | 3.6 |
| California Common | — | — | — | 6.1 | 4.6 | 5.3 |

TABLE 5-continued

Comparative turf quality[a] of 6-72-99 and other St. Augustine grasses at various locations in the U.S.

| Selection/ Variety | Turf Quality: Florida Apopka[b] | Florida Fort Lauderdale Expt 1[c] | Florida Fort Lauderdale Expt 2[d] | California SCFS[h] Expt 3[e] | California SCFS[h] Expt 4[f] | Somas[g] |
|---|---|---|---|---|---|---|
| 1081 | 7.2 | 6.1 | 5.5 | — | — | — |

[a]Quality - rated 1-10, 10 = best.
[b]Mean over 4 years with a total of 8 evaluations.
[c]Mean of 5 dates of evaluations.
[d]Mean of 15 dates of evaluations.
[e]Mean of 25 dates of evaluations.
[f]Mean of 6 dates of evaluations.
[g]Mean of 2 dates of evaluations.
[h]South Coast Field Station - University of California.

TABLE 6

Comparative turf quality[a] of 6-72-99 and other St. Augustine grasses during the winter season or early spring at various locations in the U.S.

| Selection/Variety | Turf Quality: Apopka[b] Florida | Cleveland[c] Texas | SCFS[d] California |
|---|---|---|---|
| 6-72-99 | 9.9 | 6.4 | 5.4 |
| Bitterblue | 5.0 | — | — |
| Floratam | 5.6 | 6.0 | — |
| Floratine | 5.8 | 6.0 | — |
| Raleigh | 7.7 | — | — |
| Seville | 7.8 | 6.2 | 4.5 |
| Texas Common | 8.9 | 6.2 | 4.2 |
| California Common | — | — | 4.6 |
| 1081 | 6.4 | 4.8 | — |

[a]Quality - rated 1-10, 10 = best.
[b]Mean of 3 dates of evaluations.
[c]Mean of 5 dates of evaluations.
[d]South Coast Field Station - University of California - Mean of 6 dates of evaluations.

TABLE 7

Comparative cold injury of 6-72-99 and other St. Augustine grasses in Apopka, Florida.

| Selection/Variety | Cold Injury (%) Expt. 1 | Expt. 2 | Mean |
|---|---|---|---|
| 6-72-99 | 0 | 0 | 0 |
| Bitterblue | 53 | 38 | 45 |
| Floratam | 40 | 42 | 41 |
| Floratine | 48 | 32 | 40 |
| Raleigh | 32 | 12 | 22 |
| Seville | 35 | 15 | 25 |
| Texas Common | 18 | 7 | 12 |
| 1081 | 47 | 33 | 40 |
| LSD(.05) | 20.9 | 18.5 | |

Color of turf is an important component of turf quality. 6-72-99 has a pleasing green color throughout the year. In addition, minimizing loss of green color due to herbicide injury, cold, or other causes is also important in maintaining good quality turf for 6-72-99. Besides green color or loss of green color, St. Augustine grasses have a tendency to have a purple coloring in the stem. 6-72-99 has a low level of purpling in the stems. Minimizing the number of seedheads in turf is also important in maintaining high quality turf. 6-72-99 has a medum level of flowering shoots in turf. This information is illustrated in Tables 8, 9 and 10.

TABLE 8

Comparative color ratings of 6-72-99 and other St. Augustine grasses at various locations in the U.S.

| Selection/Variety | Color[a] Florida Apopka[b] | Fort Lauderdale[c] |
|---|---|---|
| 6-72-99 | 8.9 | 1.8 |
| Bitterblue | 7.9 | 3.0 |
| Floratam | 8.4 | 2.9 |
| Floratine | 7.9 | 2.9 |
| Raleigh | 7.1 | 2.0 |
| Seville | 8.8 | 2.0 |
| Texas Common | 8.0 | — |
| California Common | — | — |
| 1081 | 8.5 | 1.3 |

| Selection/Variety | Color[a] California Somas[d] | SCFS[e] | Texas Cleveland[f] |
|---|---|---|---|
| 6-72-99 | 7.9 | 7.0 | 6.8 |
| Bitterblue | — | — | — |
| Floratam | — | — | 6.8 |
| Floratine | — | — | 6.8 |
| Raleigh | — | — | — |
| Seville | 7.5 | 8.6 | 6.7 |
| Texas Common | 5.9 | 4.2 | 6.8 |
| California Common | 7.7 | 6.5 | — |
| 1081 | — | — | 5.6 |

[a]Color rated 1-10, 10 - darkest green unless noted otherwise.
[b]Mean of 8 evaluations.
[c]Rated 1-3, 3 = darker green.
[d]Mean of 3 evaluations.
[e]South Coast Field Station
[f]Mean of 5 evaluations.

TABLE 9

Comparative ratings of various attributes of 6-72-99 and other St. Augustine grasses which detract from overall appearance.

| Selection/ Variety | Brown[a] | Dis-color[b] | Chlo-rosis[c] | Asulox[d] | Seed Heads[e] |
|---|---|---|---|---|---|
| 6-72-99 | 3.7 | 1 | 20.0 | 0 | 400 |
| Bitterblue | — | — | 14.5 | 12 | 200 |
| Floralawn | — | — | — | — | 120 |
| Floratam | 6.3 | — | 11.0 | 0 | 60 |
| Floratine | — | — | 7.5 | 2 | 80 |
| Raleigh | 8.3 | — | 10.0 | 10 | — |
| Seville | — | 0 | 17.5 | 3 | 1110 |
| Texas Common | 5.7 | 0 | 17.0 | 0 | — |
| California Common | 4.0 | 4 | — | — | — |
| 1081 | — | — | 14.5 | 7 | 650 |

[a]South Coast Field Station - University of California - Rated as % brown turf.
[b]South Coast Field Station - Rated as % discolored turf.
[c]Apopka, Florida - Rated as % chlorotic turf.
[d]Apopka, Florida - Rated as % injury.
[e]Fort Lauderdale, Florida - Rated as the number of seedheads per square meter.

TABLE 10

Comparative evaluations of purple stem color of 6-72-99 and other St. Augustine grasses.

| Selection/ Variety | Purple Stem Color[a] Ohio Marysville[b] | Florida Fort Lauderdale | Apopka | California SCFS |
|---|---|---|---|---|
| 6-72-99 | 3.5 | 4.5 | 5 | 0.7 |
| Bitterblue | 8.0 | 5.3 | 30 | — |
| Floratam | 8.3 | 6.1 | 33 | 2.7 |

TABLE 10-continued

Comparative evaluations of purple stem color of 6-72-99 and other St. Augustine grasses.

| Selection/ Variety | Purple Stem Color[a] Ohio Marysville[b] | Florida Fort Lauderdale | Apopka | California SCFS |
|---|---|---|---|---|
| Floratine | 8.0 | 6.3 | 10 | — |
| Raleigh | 6.0 | 4.0 | 14 | 1.7 |
| Seville | 4.0 | 4.5 | 1 | — |
| Texas Common | 4.5 | — | 9 | 1.0 |
| 1081 | 7.5 | 5.9 | 52 | — |
| LSD(.05) | 1.1 | | | 0.9 |

[a]Purple stem color rated 1-10, 10 = stolons are very purple, 1 = stolons are entirely green. For Apopka, visual estimation of the level of stem purpling in percent.
[b]Test planted in the greenhouse.

Tolerance to various diseases and insects is important for maintaining good quality turf with minimum levels of pesticides. 6-72-99 has shown resistance to St. Augustine grass Decline Virus inoculations in the laboratory. In field studies, it has shown a good level of resistance to gray leaf spot (*Pyricularia grisea*) and dollarspot (Curvularia sp.). Tolerance to insects is an extremely difficult characteristic to measure accurately. For chinchbugs (Blissus sp.) and sod webworm (Crambus sp.), 6-72-99 has shown tolerance levels equal to most other St. Augustine grasses.

TABLE 11

Comparative disease ratings of 6-72-99 and other St. Augustine grasses.

| Selection/ Variety | Gray Leaf Spot[a] Apopka[b] Florida | Fort Lauderdale[c] Florida | Dollarspot[d] Fort Lauderdale Florida |
|---|---|---|---|
| 6-72-99 | 1.0 | 4.0 | 0.0 |
| Bitterblue | 3.5 | 6.6 | 0.2 |
| Floratam | 3.8 | 4.0 | 0.0 |
| Floratine | 2.6 | 7.0 | 0.5 |
| Raleigh | 0.7 | 3.6 | — |
| Seville | 0.8 | 3.8 | 0.0 |
| Texas Common | 2.4 | — | — |
| 1081 | 2.2 | 2.7 | 0.3 |

[a]Rated 1-10, 10 = most disease.
[b]Mean of two evaluations.
[c]Mean of two evaluations.
[d]Rating based on number of spots per square meter.

TABLE 12

Comparative ratings of insect tolerance of 6-72-99 and other St. Augustine grasses.

| Selection/Variety | Chinchbugs[a] Florida[c] | California[d] | Sod Webworms[b] Florida[e] |
|---|---|---|---|
| 6-72-99 | 2.0 | 0.0 | 49 |
| Bitterblue | 5.0 | — | 24 |
| Floratam | 7.0 | — | 18 |
| Floratine | 2.7 | — | 24 |
| Raleigh | 6.3 | — | 44 |
| Seville | 5.7 | 0.3 | 39 |
| Texas Common | 4.7 | 2.0 | — |
| California Common | — | 3.0 | — |

[a]Rated 1-10, 10 = severe damage.
[b]Rated as % damage.
[c]Planted in the greenhouse at Apopka, Florida.
[d]South Coast Field Station, University of California.
[e]Planted in containers at Fort Lauderdale, Florida. Mean of two evaluations.

What is claimed is:

1. A St. Augustine grass, substantially as herein illustrated and described.

* * * * *